United States Patent
Aihara et al.

(10) Patent No.: US 7,963,923 B2
(45) Date of Patent: Jun. 21, 2011

(54) BLOOD PRESSURE METER

(75) Inventors: Kimihisa Aihara, Fujisawa (JP);
Shoichi Hayashida, Hitachinaka (JP);
Shinji Mino, Atsugi (JP); Hiroshi Koizumi, Atsugi (JP); Naoe Tatara, Isehara (JP); Taisuke Oguchi, Mito (JP); Junichi Shimada, Iruma (JP)

(73) Assignee: Nippon Telegraph and Telephone Corporation, Tokyo (JP)

( * ) Notice: Subject to any disclaimer, the term of this patent is extended or adjusted under 35 U.S.C. 154(b) by 0 days.

(21) Appl. No.: 11/661,767

(22) PCT Filed: Oct. 4, 2005

(86) PCT No.: PCT/JP2005/018370
§ 371 (c)(1),
(2), (4) Date: Mar. 5, 2007

(87) PCT Pub. No.: WO2006/038628
PCT Pub. Date: Apr. 13, 2006

(65) Prior Publication Data
US 2008/0097228 A1    Apr. 24, 2008

(30) Foreign Application Priority Data
Oct. 6, 2004  (JP) .................................. 2004-294301

(51) Int. Cl.
*A61B 5/02*  (2006.01)
(52) U.S. Cl. ...................................... 600/490; 600/485
(58) Field of Classification Search ................. 600/485, 600/490
See application file for complete search history.

(56) References Cited

U.S. PATENT DOCUMENTS

| 3,412,729 | A | * | 11/1968 | Smith, Jr. ...................... 600/324 |
| 3,810,460 | A | | 5/1974 | Van Nie |
| 4,334,544 | A | * | 6/1982 | Hill et al. ....................... 600/473 |
| 4,821,734 | A | * | 4/1989 | Koshino ......................... 600/493 |
| 5,413,101 | A | * | 5/1995 | Sugiura ......................... 600/323 |
| 2002/0082508 | A1 | * | 6/2002 | Ogura et al. .................. 600/490 |
| 2002/0120201 | A1 | * | 8/2002 | Chio et al. .................... 600/490 |
| 2003/0036685 | A1 | | 2/2003 | Goodman |
| 2003/0060721 | A1 | * | 3/2003 | Nakazawa et al. ............ 600/490 |
| 2004/0176692 | A1 | | 9/2004 | Kario et al. |
| 2004/0267103 | A1 | * | 12/2004 | Li et al. .......................... 600/323 |
| 2006/0287590 | A1 | * | 12/2006 | McEowen ...................... 600/331 |

FOREIGN PATENT DOCUMENTS

| EP | 0 073 123 A2 | 3/1983 |
| EP | 0 678 277 A1 | 10/1995 |
| JP | 61 193643 | 8/1986 |
| JP | 4 256727 | 9/1992 |
| JP | 9 122083 | 5/1997 |
| JP | 10 286241 | 10/1998 |
| JP | 2001 70260 | 3/2001 |
| TW | 415229 | 12/2000 |
| TW | M242734 | 9/2004 |
| WO | WO 03/073924 | 9/2003 |

* cited by examiner

*Primary Examiner* — Patricia C Mallari
*Assistant Examiner* — Christian Jang
(74) *Attorney, Agent, or Firm* — Oblon, Spivak, McClelland, Maier & Neustadt, L.L.P.

(57) ABSTRACT

A blood-pressure meter having storing means for storing a blood pressure measurement result, and time measurement means for measuring a time is disclosed. The blood-pressure meter includes: input means for entering behavior history; means for storing the blood pressure measurement result into the storing means while associating the blood pressure measurement result with a time when blood pressure measurement is performed; and means for storing the entered behavior history into the storing means while associating the behavior history with a time corresponding to the behavior history.

9 Claims, 11 Drawing Sheets

HOLDING PART

MEASURING PART

| MIDDLE ITEMS | ENTRY ITEMS |
|---|---|
| DRUG-TAKING | DRUG-TAKING |
| DAILY BEHAVIOR | UPRISE, EMICTION, DEFECATION, DIET, ALCOHOL DRINKING, BATH, DAYTIME NAP, SLEEP CONVERSATION, REST, ENTERTAINMENT |
| HOUSEHOLD CHORES | SHOPPING, CLEANING, LAUNDRY, COOKING |
| MOVE | BUS, TRAIN, AIRPLANE, SHIP, WALK, RUN, BICYCLE, MOTORCYCLE, DRIVING, STAIR UP AND DOWN, |
| WORK | WORK |
| EXERCISE | EXERCISE |

FIG.11

BLOOD PRESSURE METER

TECHNICAL FIELD

The present invention relates to a blood-pressure meter. More particularly, the present invention relates to a blood-pressure meter including a function for recording behavior history.

BACKGROUND ART

As the population is aging, response to lifestyle-related diseases of adults is becoming a large public problem. Especially, as to diseases related to high blood pressure, it is recognized that collecting blood pressure data for a long term is very important. From this viewpoint, various measurement apparatuses for measuring living body information such as the blood pressure are being developed. Among such apparatuses, a portable patient monitoring apparatus is proposed in which an ear is selected as a wearing position where daily living and behavior are not disturbed, that is, the patient monitoring apparatus is inserted into an external auditory meatus or other part of the external ear so as to be worn continuously (refer to patent document 1, for example).

This apparatus calculates blood pressure, and pulse, pulse wave, electrocardiogram, body temperature, arterial oxygen saturation and the like based on a received light amount of scattered light of infrared light or visible light that is radiated into the living body. Since various living body data can be measured only by wearing the apparatus by inserting it into the external auditory meatus, the apparatus is considered to be one that can automatically monitor physical status of the patient practically without restricting flexibility of physical activity of the patient.

Living body information measurement for pulse, pulse wave, arterial oxygen saturation and the like can be relatively easily realized using a photoelectric sensor and an electric circuit since it is only necessary to measure a pulse wave signal of a blood vessel part or an absorption spectrum of blood. On the other hand, for measuring blood pressure, since it is necessary to ascertain pulse wave that changes while increasing or decreasing a pressure applied to a measured part of a living body, it is generally necessary to provide a blood-pressure measurement apparatus with a cuff for increasing or decreasing a pressure onto the measured part and an air system that includes a pump and a valve for supplying and discharging air in the cuff.

In addition, among blood pressure measurement apparatuses, there is a blood pressure measurement apparatus (A&D company, TM2431, for example) that measures and records blood pressure on an upper arm 24 hours in a row. The blood pressure measurement apparatus is used as a means and the like for determining what sort of hypotensive drug should be taken in what way for obtaining most effective treatment.

[Patent document 1] Japanese Laid-Open Patent Application No. 9-122083

DISCLOSURE OF THE INVENTION

Problem to be Solved by the Invention

One of objectives for measuring the blood pressure continuously as described above is to obtain blood pressure values corresponding to various behaviors in a daily life. However, in the conventional techniques, behaviors of a measurement subject are recorded by the measurement subject himself/herself by writing down the behaviors on a paper. The method for recording the behaviors on a paper is not only cumbersome itself, but also there is a problem in the method that relationship between a behavior and a blood pressure measurement result cannot be ascertained instantly so that time and effort are necessary for diagnosis.

The present invention is contrived in view of the above points, and an object of the present invention is to provide a blood-pressure meter that enables to easily ascertain the relationship between the behavior and the blood pressure measurement result.

Means for Solving the Problem

The problem is achieved by a blood-pressure meter including storing means for storing a blood pressure measurement result, and time measurement means for measuring a time, the blood-pressure meter including: input means for entering behavior history; means for storing the blood pressure measurement result into the storing means while associating the blood pressure measurement result with a time when blood pressure measurement is performed; and means for storing the entered behavior history into the storing means while associating the behavior history with a time corresponding to the behavior history. By the way, the time corresponding to the behavior history may be a time which the blood-pressure meter automatically add as a time when the behavior history is entered, or may be a time entered by a measurement subject as a time when the behavior is performed.

The blood-pressure meter may further include display means for displaying candidates for being entered as the behavior history, and the blood-pressure meter may perform blood pressure measurement at predetermined time intervals by measuring the predetermined time intervals by the time measuring unit.

The blood-pressure meter may further include search means for searching blood pressure measurement results and behavior history stored in the storing unit based on a condition entered from the input means to extract data satisfying the condition. More particularly, the search means may extract a blood pressure value corresponding to behavior information entered from the input means, also, the search means can extract behavior history corresponding to a blood pressure value entered from the input means.

In addition, the present invention may be configured as a program for causing a blood-pressure meter comprising storing means for storing a blood pressure measurement result and time measurement means for measuring a time to function as behavior history processing means, the behavior history processing means including: input means for entering behavior history; means for storing the blood pressure measurement result into the storing means while associating the blood pressure measurement result with a time when blood pressure measurement is performed; and means for storing the entered behavior history into the storing means while associating the behavior history with a time corresponding to the behavior history.

Effect of the Invention

According to the present invention, since behavior history is entered, and the entered behavior history is stored in storing means being associated with a time of the behavior history, a blood pressure meter can be provided in which relationship between behavior and a blood pressure measurement result can be ascertained easily.

EXPLANATION OF REFERENCE SIGNS 1 tragus, 2 antitragus, 3 concha auriculae, 4 antihelix, 5 helix, 6 crus anthelicis, 7 crus helicis, 8 cavum conchae, 31 first arm, 32 second arm, 33, 34 cuff, 35 spindle, 36 air tube, 37 signal line, 40 distance variable mechanism, 41 rotation mechanism, 61 light-emitting element, 62 light-receiving element, 10 auricle, 11 external ear, 12 external auditory meatus, 15 frame, 16 holding part, 17 sensing unit, 18 suspension part

Preferred Embodiments for Carrying out the Invention

In the following, embodiments of the present invention are described with reference to figures. In the following, a basic configuration of an ear-type blood-pressure meter is described, and after that, a configuration for recording behavior history, and further, a configuration for starting blood pressure measurement based on a degree of activity are described.

(Basic Configuration of the Ear-type Blood-pressure Meter)

First, structure and names of each part of an auricle related to descriptions of the era-type blood-pressure meter are described with reference to a structural drawing of the auricle shown in FIG. 1.

Figure 1:
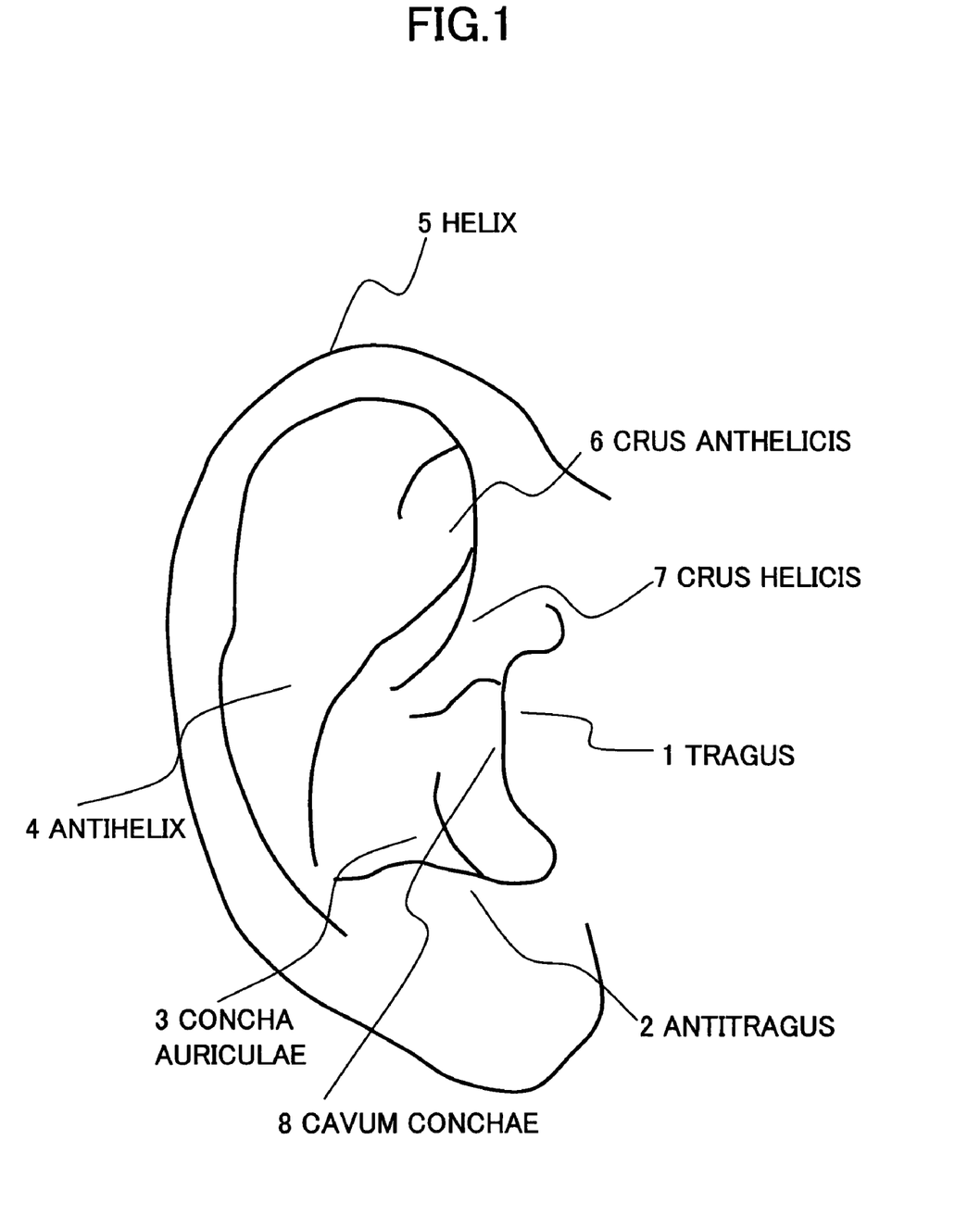
FIG. 1 is a component drawing of an auricle.

The auricle is a so-called ear, and is a general term of the whole of the ear shown in FIG. 1. The parts of the auricle are called a tragus 1, an antitragus 2, a concha auriculae 3, an antihelix 4, a helix 5, a crus anthelicis 6, a crus helicis 7, and a cavum conchae 8 respectively. In this application, "inside of tragus" means a side of the cavum conchae 8 in the tragus 1 shown in FIG. 1, and "outside of tragus" means a side opposite to the cavum conchae 8 in the tragus 1 shown in FIG. 1. In addition, the ear including the auricle and the external auditory meatus is called an external ear. A periphery of the base of the auricle in the temporal region is called a periphery of external ear, and "ear part" in the present specification and claims means a part including the external ear and the periphery of the external ear. A branch artery exists in a subcutaneous part of the auricle and the external auditory meatus. In addition, in the periphery of the base of the auricle in the temporal region, a superficial temporal artery that appears on a surface layer of skin and that extends upward exists. These are useful parts for measuring a pulse wave (measuring a blood pressure).

Figure 2A:
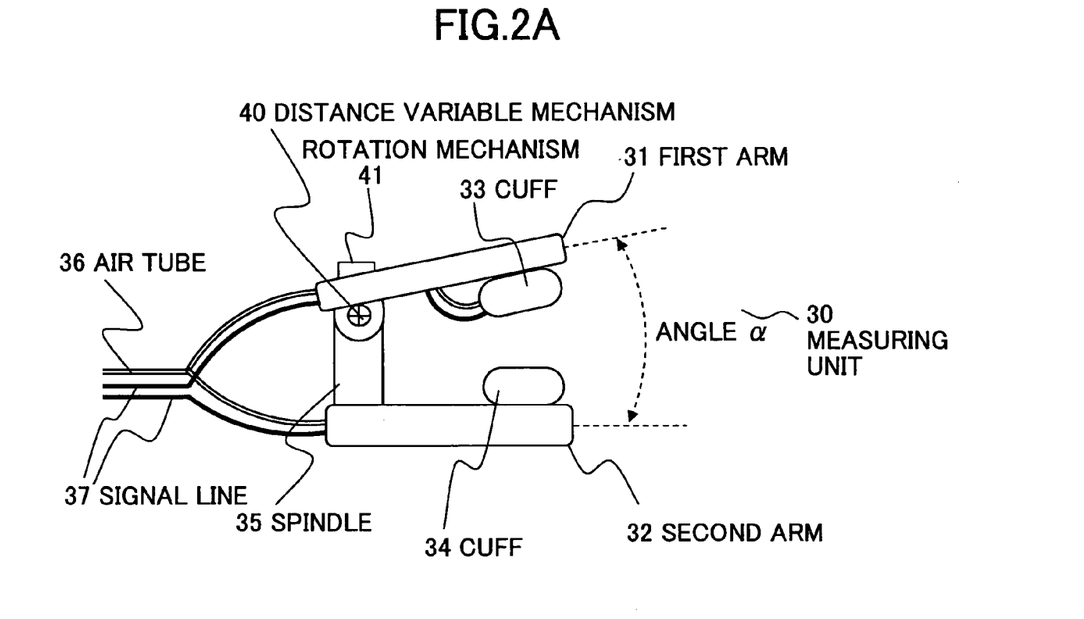
FIG. 2A is a drawing showing a configuration example of a measuring unit 30 of an ear-type blood-pressure meter.
Figure 2B:
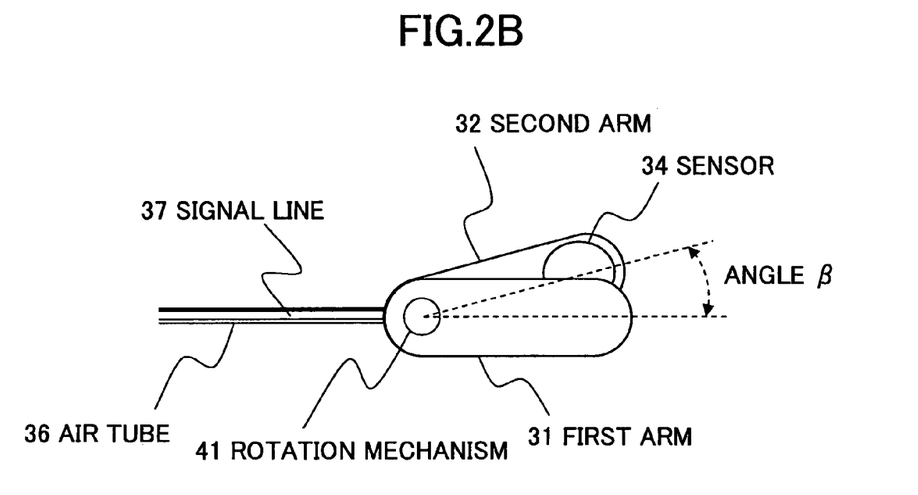
FIG. 2B is a drawing showing a configuration example of the measuring unit 30 of the ear-type blood-pressure meter.

FIGS. 2A and 2B are drawings showing a configuration example of a measuring unit 30 of the ear-type blood-pressure meter of this embodiment. FIG. 2A is a front view, and FIG. 2B is a plan. In FIGS. 2A and 2B, 31 indicates a first arm, 32 indicates a second arm, 33 and 34 indicate cuffs respectively, 35 indicates a spindle, 36 indicates an air tube (hollow tube), 37 indicates a signal line, 40 indicates a distance variable mechanism, 41 indicates a rotation mechanism, and the cuff 33 includes in the inside a photoelectric sensor including a light-emitting element and a light-receiving element.

The air tube 36 for supplying and discharging air for each of the cuffs 33 and 34, and signal lines 37 for sending and receiving a signal for the photoelectric sensor are connected to the measuring unit 30. Each of the air tube 36 and the signal line 37 goes through the first arm 31 and the second arm 32, and is drawn out of the other end. The destination of the connection of each of the air tube and the signal line is a main body unit in which an air supplying and discharging system and an electronic circuit system are included in one case.

The measuring unit 30 includes the first arm 31, the second arm 32, and the spindle 35, in which one end of each of the first arm 31 and the second arm 32 is connected to the spindle 35. In addition, the measuring unit 30 includes the distance variable mechanism, for adjusting an interval between other ends of the first arm 31 and the second arm that are opposed to each other, at a part at which each of the first arm 31 and the second arm 32 is connected to the spindle 35, or at the spindle 35.

In the configuration example of the measuring unit 30 shown in FIG. 2A, as a variable mechanism for changing a distance between surfaces on which the first arm 31 and the second arm are opposed to each other, the measuring unit 30 has a function for adjusting the interval between the surfaces on which the first arm 31 and the second arm 32 are opposed to each other by changing an angle between the spindle 35 and the first arm 31 so as to change the angle α shown in FIG. 2A. As a mechanism for making the angle adjustable in the distance variable mechanism 40, any mechanism can be adopted such as a mechanism for adjusting the angle between the spindle 35 and the first arm 31 using a screw, a mechanism for using friction together with screw fixing and the like. Further, a mechanism for expanding and contracting the length of the spindle 35 can be used as a mechanism for adjusting the interval of the other ends at which the first arm 31 and the second arm 32 are opposed to each other. In addition, the measuring unit 30 shown in FIG. 2A includes the rotation mechanism 41, for rotating the first arm 31 using the spindle 35 as an axis, at a part at which the first arm 31 is connected to the spindle 35. The rotation mechanism 41 includes a function for changing an angle β between orientation of the first arm 31 and orientation of the second arm 32 when being viewed from an axial direction of the spindle 35 shown in FIG. 2B. By the way, it is optional to provide the rotation mechanism 41.

Figure 3:
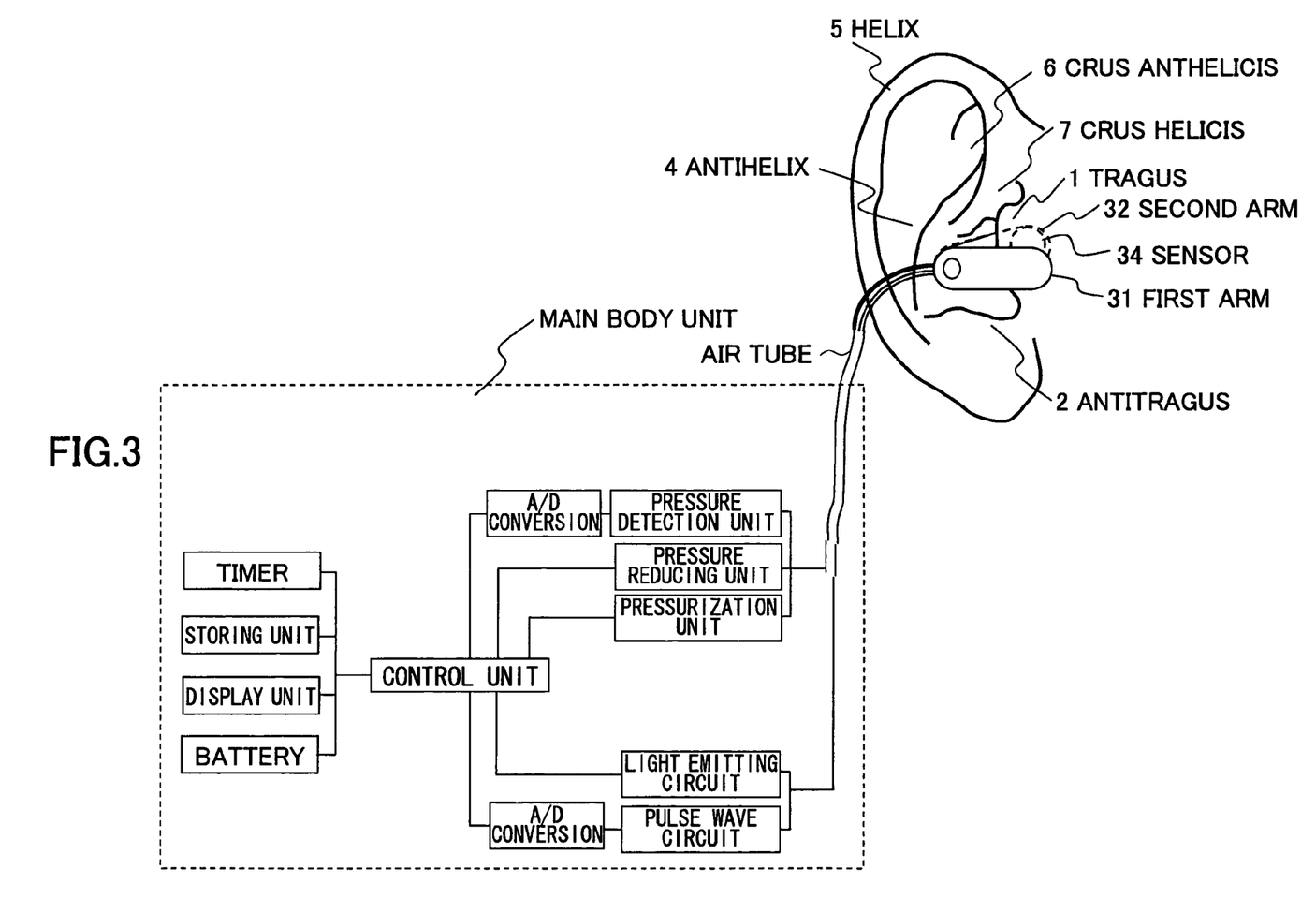
FIG. 3 is a drawing showing an example for wearing the ear-type blood presser meter on the auricle and a configuration of an main body unit.

The measuring unit 30 has a function for detecting pulse wave information by bringing the cuffs 33 and 34 into contact with a part of a protruding portion in the auricle of the human body, for example, contact with both sides of the tragus 1 of the auricle. FIG. 3 shows an example in which the ear-type blood presser meter is worn on the auricle. As shown in FIG. 3, the measuring unit 30 is worn so as to be brought into contact with the tragus 1 from both sides. The measuring unit 30 is worn so that the cuff 33 of the first arm 31 contacts the outside of the tragus 1 and the cuff 34 of the second arm 32 contacts the inside of the tragus 1. A part of the second arm 32 and the cuff 34 are drawn with dotted lines since they exists in the inside of the tragus 1.

When bringing the cuff 33 and the cuff 34 into contact with the both sides of the tragus 1, the interval between the cuffs is adjusted into a proper contacting state by changing the interval between the opposed surfaces of the first arm 31 and the second arm 32 by the distance variable mechanism 40. In addition, the positions which the cuff 33 and the cuff 34 contact are properly adjusted by changing the angle $\beta$ shown in FIG. 2B by the rotation mechanism 41. By the way, when wearing the measuring unit 30 on the tragus, wearing stability is bad only by pinching the tragus with the cuffs 33 and 34 like this example. For this reason, a sponge material and the like is provided on the back side of the second arm 32 in an integrated manner, in which the sponge material has a shape that almost fills in a space between the second arm 32 and the concha auriculae 3 when wearing the cuff 34 contacting the inside of the tragus 1. Accordingly, the measuring unit 30 is multiply-supported such that the cuff part contacts the surface of the tragus and that the sponge material contacts and fits into the concha auriculae 3, so that the whole of the measuring unit 30 is worn on the ear stably.

As shown in FIG. 3, the main body unit includes an air system including a pressurization unit for supplying air to the cuff to expanding the cuff, a pressure reducing unit for reducing pressure from the cuff by discharging air from the expanded cuff at a predetermined rate, and a pressure detection unit for detecting pressure in the cuff. In addition to the air system, the main body unit includes a light-emitting circuit for driving the light-emitting element, a pulse wave circuit for detecting a pulse wave signal obtained by artery radiation by the light-emitting element, and a control unit for controlling these. These configuration units are implemented in one case densely, so that the main body unit has a size such that it can be put in a breast pocket. The main body unit further includes a display unit, a storing unit, a timer and a battery and the like. The storing unit is a memory, for example. In the following, it is assumed that the storing unit is a memory. In addition, the display unit is a liquid crystal panel, or a number display device of seven segments or the like. Details of the battery and the memory are described later. In addition, as described later, the main body unit also includes an input unit and a search unit.

Figure 4:
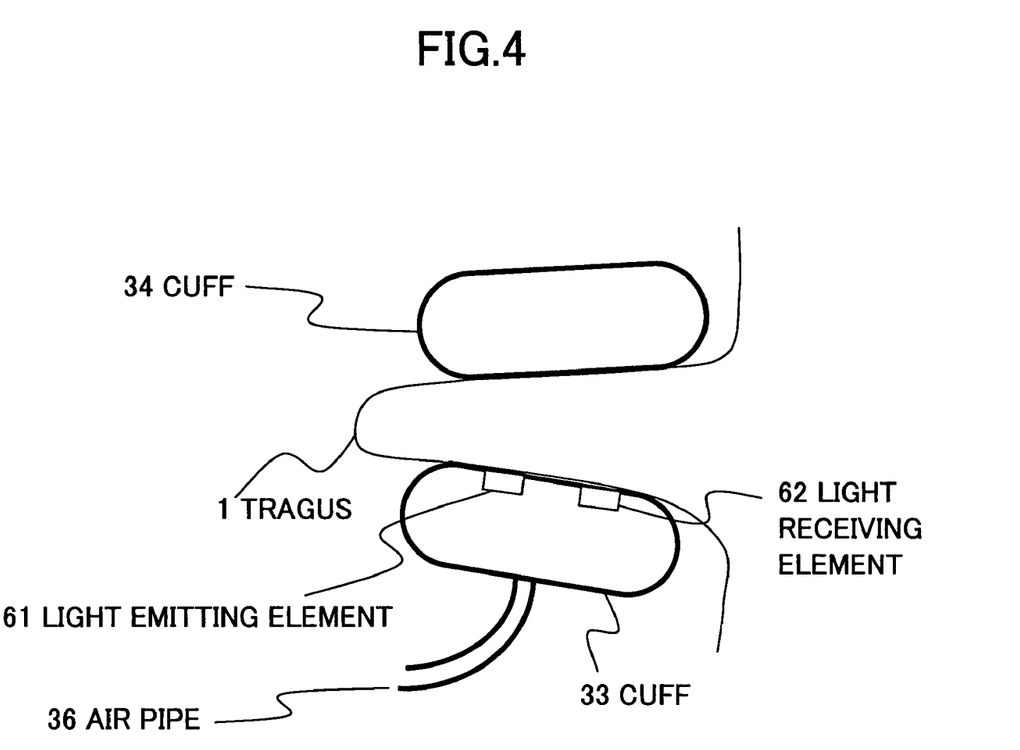
FIG. 4 is a drawing showing an example of a photoelectric sensor placed in the cuff.

FIG. 4 indicates an example of the photoelectric sensor placed in the cuff. As shown in FIG. 4, a light-emitting element 61 and a light-receiving element 62 are placed on a side where the cuff 33 contacts the tragus 1, so that, light emitted by the light-emitting element 61 is entered in the tragus 1 as incident light that is scattered by blood vessels in the tragus 1 or blood corpuscles in the blood vessels, and the scattered light 66 is received by the light-receiving element 62. The incident light enters the tragus 1 from the light-emitting element 61 and the incident light is scattered in the tragus 1, and the light-receiving element 62 is placed at a position so as to receive the scattered light 66.

By using such light-emitting and light-receiving element pair, a so-called pulse wave that is a waveform due to blood vessel vibrations occurred in conjunction with expansion and contraction of the heart can be detected. Then, in the process for detecting the pulse wave, air pressure of the cuffs are gradually decreased from a state in which blood flow in the blood vessel is stopped by pressing the tragus 1 using the cuffs 33 and 34, and a pulse wave corresponding to the pulsation of the blood vessel is measured as a pulse wave signal in the process for decreasing the air pressure so that the blood pressure can be measured from the pulse wave signal.

In FIG. 4, the light-emitting element 61 and the light-receiving element 62 are not necessarily placed on the expanding side of the cuff 33. But, by fixing the light-emitting element 61 and the light-receiving element 62 on the expanding side of the cuff 33, the cuff 33 and the light-emitting element 61, and the cuff 33 and the light-receiving element 62 move together when supplying pressure to the tragus by supplying air into the cuff 33 and when reducing the pressure applied on the tragus 1 by discharging the air from the cuff 33 and the cuff 34, so that position relationship among the cuff 34, the light-emitting element 61 and the light-receiving element 62 becomes stable. Therefore, the pulse wave can be detected more accurately, so that the blood pressure can be measured more accurately from the detected pulse wave.

Although FIG. 4 shows a reflection type in which the pair of the light-emitting element and the light-receiving element are placed in the cuff 33 so as to detect light scattered in a reflection direction of radiating light, a transmission type can be used in which the light-emitting element is placed in the cuff 33 and the light-receiving element is placed in the cuff 34 so as to detect light scattered in a transmitting direction of the radiating light. In addition, for each type, the positions of the light-emitting element and the light-receiving element can be reversed, for example, that is, placement of the light-emitting element and the light-receiving element can be properly determined.

Figure 5:
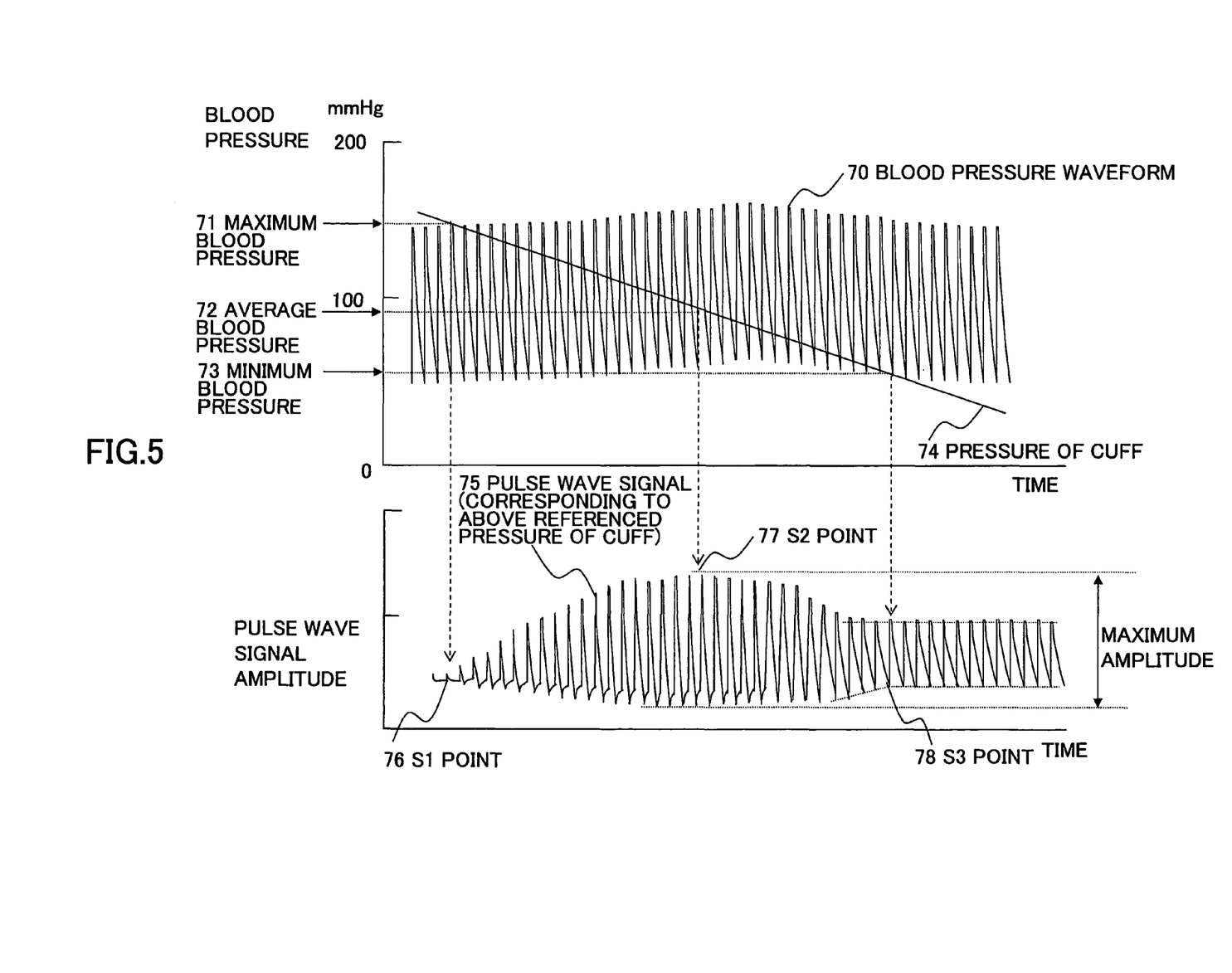
FIG. 5 is a drawing showing relationship among a pressure 74 of the cuff, a pulse wave signal 75 corresponding to pulsation of blood vessel, and a blood pressure waveform 70.

FIG. 5 shows relationship among a cuff pressure 74 applied by the cuffs 33 and 34, and a pulse wave signal 75 corresponding to pulsation of blood vessels, and a blood pressure waveform 70.

As shown in the blood pressure waveform 70 in FIG. 5, the blood pressure changes like gentle undulation in whole while showing a sawtooth waveform due to heart action. This blood pressure waveform 70 is shown for the sake of explanation of the principle of blood pressure measurement, and can be measured by a precision blood pressure measuring device inserted into a blood vessel.

The cuff pressure 74 shown in FIG. 5 shows a case in which the cuff pressure is gradually decreased as time passes by discharging air in the cuff gradually from a state in which blood flow is stopped by applying adequately high pressure to the tragus 1 by supplying air into the cuff. A waveform of the pulse wave measured in the decreasing process of the cuff pressure 74 shown in FIG. 5 is shown as the pulse wave signal 75. As shown in FIG. 5, when the cuff pressure 74 is adequately high, the blood flow stops so that the pulse wave signal 75 scarcely appears. But, as the cuff pressure 74 decreases, a small triangle-like pulsation waveform appears as the pulse wave signal 75. A time point when the pulse wave signal 75 appears is shown as S1 point 76. Further, as the cuff pressure 74 decreases, the amplitude of the pulse wave signal 75 increases so that it becomes the maximum value at S2 point 77. As the cuff pressure 74 further decreases, after the amplitude of the pulse wave signal 75 gradually decreases, the top part of the pulse wave signal 75 becomes constant to show flat state. After a little time delay, the bottom part of the pulse wave signal 75 also changes to a constant value. A time point when the value of the bottom part of the pulse wave signal 75 changes to the constant value is shown as S3 point

78. It is kwon that, in the decreasing process of the cuff pressure 74, a value of the cuff pressure 74 corresponding to the S1 point 76 is the maximum blood pressure 71, the value of the cuff pressure 74 corresponding to S2 point 77 is the average blood pressure 72, and the value of the cuff pressure 74 corresponding to the S3 point 78 is the minimum blood pressure 73.

As mentioned above, in the process in which the cuff pressure 74 is decreased from the high pressure by which blood flow in the blood vessels stops, the pulse wave signal 75 changes so that it shows distinctive shapes. Thus, for example, by storing shapes of the pulse wave signal 75 corresponding to each blood pressure of each time point, a position at which a blood pressure value exists between the maximum blood pressure and the minimum blood pressure can be known from a pulse wave signal 75 measured at any time point. In addition, the pulse wave signal 75 shows especially distinguished waveform change at the S1 point 76 corresponding to the maximum blood pressure 71, the S2 point 77 corresponding to the average blood pressure 72 and the S3 point 78 corresponding to the minimum blood pressure 73. Thus, by storing characteristics of the changes of the waveforms, blood pressure can be also measured from the characteristics of the changes of the waveforms. For example, the average blood pressure 72 can be continuously measured by controlling the cuff pressure 74 such that the pulse wave signal 75 keeps the maximum value at the time when the S2 point corresponding to the average blood pressure 72 is measured in which the amplitude of the pulse wave signal 75 becomes maximum. By the similar principle, continuous measurement is possible for the maximum blood pressure 71 and the average blood pressure 72.

The above mentioned example is an example in which the maximum blood pressure and the minimum blood pressure are obtained by detecting volume pulse wave using the photoelectric sensor. By changing the photoelectric sensor to a piezoelectric sensor, the ear-type blood-pressure meter can be configured as a pressure pulse wave type for detecting the pulse wave signal by pushing the piezoelectric sensor to the tragus. In addition, by changing the photoelectric sensor to a small microphone, the ear-type blood-pressure meter can be configured as a Korotkoff type. Further, a vibration sensor can be used for detecting a pulse wave from vibration of the cuff. In addition, as a means for applying pressure to the ear, a mechanical mechanism such as an actuator can be used other than the mechanism using air like cuff.

Figure 6:
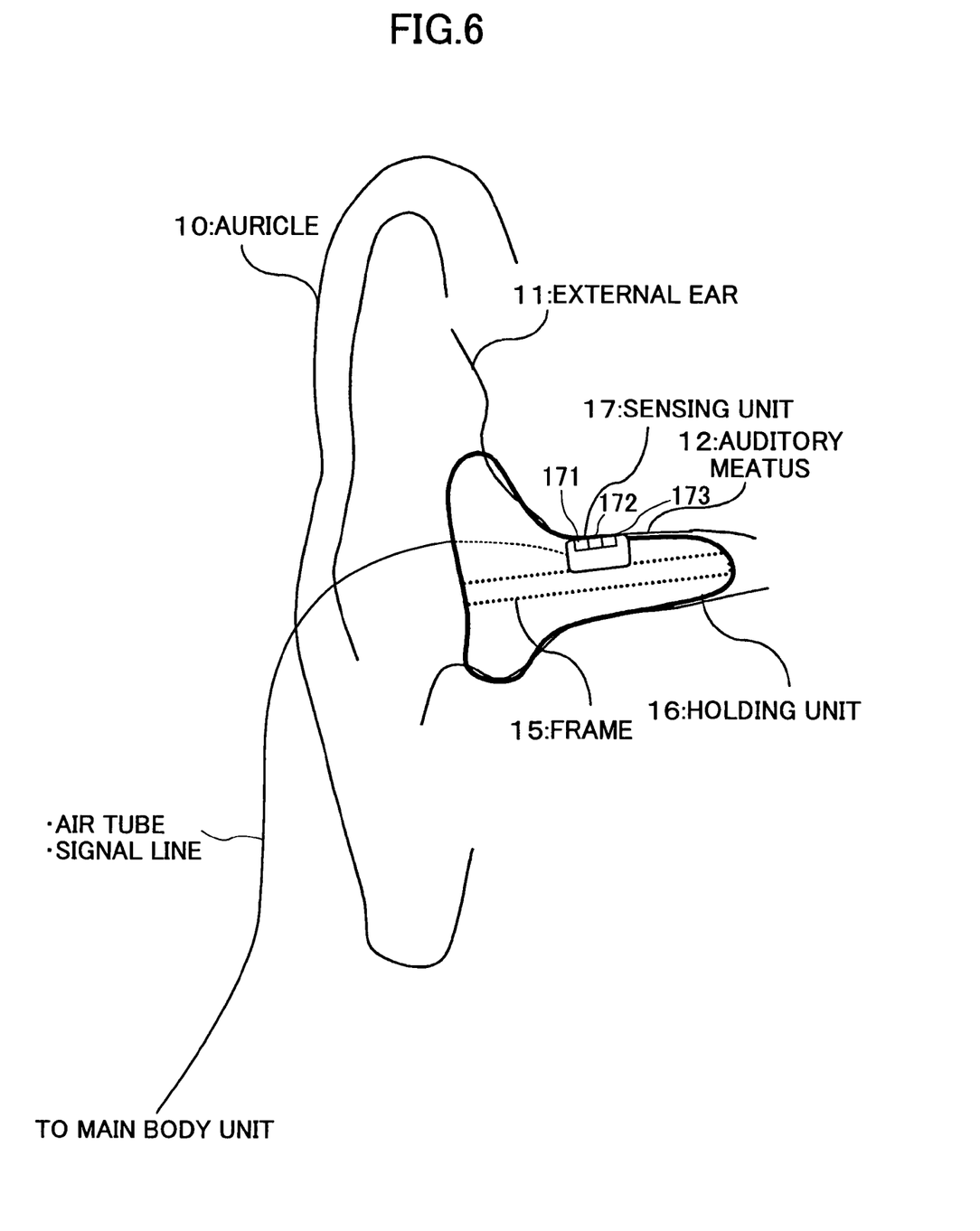
FIG. 6 is a drawing showing another embodiment of the measuring unit of the ear-type blood-pressure meter.

As the ear-type blood-pressure meter that is a basis of this embodiment, other than the ear-type blood-pressure meter for measuring blood pressure by pinching a part of the auricle with the above-mentioned arms, an ear-type blood-pressure meter used by inserting a measuring unit into the external auditory meatus shown in FIG. 6 can used. The measuring unit of the blood-pressure meter shown in the figure includes a hollow frame 15, a holding part 16 for holding the hollow frame 1 in the external auditory meatus, and a sensing part 17 that is attached to the hollow frame 1. FIG. 6 shows a state in which the holding part 16 is worn in the external ear 11. For manufacturing the holding part, a shape of the external ear 11 and the external auditory meatus 12 of a measurement subject is made with polymer resin impression material and the like. Then, based on this model, a whole shape is made with silicone resin and the like, for example. Further, a part is hollowed for keeping a route of sound so as to form the frame 15 and the sensing part 17 is placed. The sensing part includes a light-emitting element 171, a light-receiving element 172 and a pressure generation mechanism 173, and is connected to the main body unit with the air tube and signal lines and the like shown in FIG. 3. By this blood-pressure meter, blood pressure is measured by pressing artery of the external auditory meatus. By the way, principle for measuring the blood pressure is the same as that of the blood-pressure meter shown in FIG. 3.

Figure 7A:
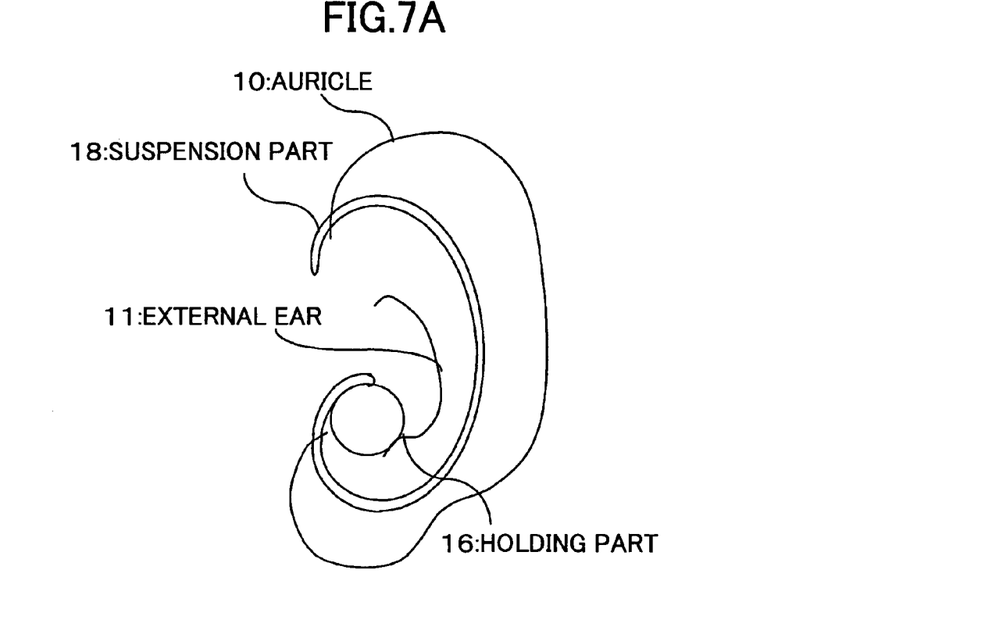
FIG. 7A is a drawing showing an example of a suspension part of the measuring unit.
Figure 7B:
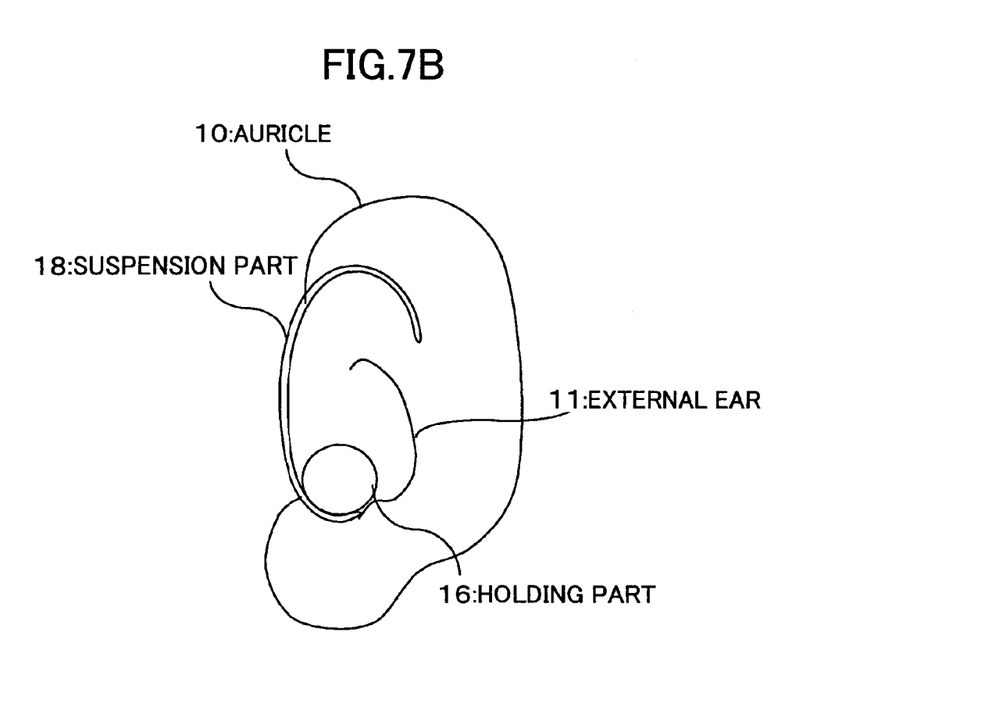
FIG. 7B is a drawing showing an example of a suspension part of the measuring unit.

In addition, as shown in FIGS. 7A and 7B, a suspension part 18 for suspending the holding part 16 from the external ear 11 may be provided. The shape of the suspension part 18 may be one that surrounds the auricle 10 to the occipital side as shown in FIG. 7A. Alternatively, the shape may be one that surrounds the auricle 10 to the face side as shown in FIG. 7B, or may be a circle-like shape or a linear shape.

Figure 8:
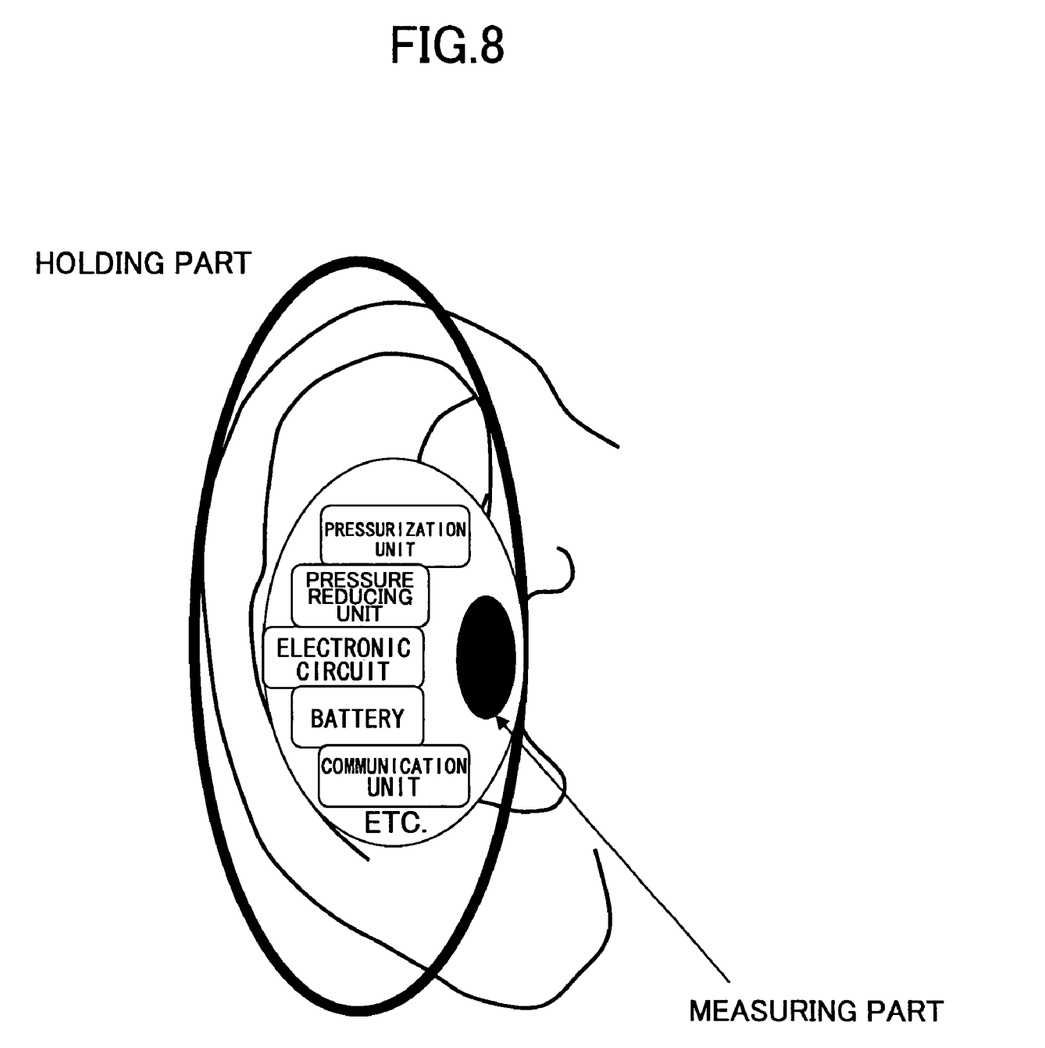
FIG. 8 is a drawing showing an example in a case where the measuring unit and the main body unit are integrated.

In each ear-type blood-pressure meter, instead of providing the main body unit and the measuring unit separately, the main body unit and the measuring unit can be integrated as shown in FIG. 8. In this case, the air tube for connecting between the main body unit and the measuring unit is unnecessary. By the way, although FIG. 8 shows an example of a type for inserting into the external auditory meatus, also the blood-pressure meter shown in FIG. 3 can be configured such that the main body unit and the measuring unit are integrated by attaching the main body unit to the arm, for example.

DETAILED CONFIGURATION EXAMPLE

Since the above-mentioned ear-type blood-pressure meter includes a battery, a memory and a timer, it is possible to measure blood pressure for at least 24 hours at predetermined time intervals and continue to store measured values. Following is the operation for measuring blood pressure at predetermined time intervals.

A predetermined time interval is stored in the storing unit beforehand. Then, the control unit controls the light-emitting circuit, the pressurization unit and the pressure reducing unit and the like so as to measure blood pressure each time when detecting a predetermined time by referring to the predetermined time interval and the timer. The result of the blood pressure measurement is stored in the storing unit while the result being associated with the measurement time. In addition to storing the result, a blood pressure value and a pulse and the like at the time are displayed on the display unit (liquid crystal panel, number display device of seven segments, for example). It is also possible to display blood pressure values in chronological order after completing blood pressure measurement.

In the following, a detailed configuration example is described in view of measuring at least 24 hours, continuing to store the measurement values and using the stored data.

As a battery used in the main body unit, a chargeable battery is used, and a connector for changing is provided in the main body unit. As the chargeable battery, there are a Li ion battery and a Ni—Cd battery and the like. By using such a chargeable battery, a blood-pressure meter applicable for continuous measurement can be provided. By the way, by providing a battery box such that a battery can be changeable, the main body unit can be also configured to use an AAA, AA, C-size, D size, 0006P or button battery or the like.

Further, instead of using a battery, the main body unit may be provided with an electric power generation unit such that power is supplied from the electric power generation unit to each functional unit. As the electric power generation unit, it is possible to use an alcoholic battery or a fuel cell or the like.

As the memory, a detachable memory may be used, and the main body unit may be configured to be provided with a memory slot for the memory to be detachable. As the memory, a memory for a personal computer such as a USB memory, a SD card, a PCMCIA card, and a memory stick can be used. By using such a detachable memory, measurement data can be easily moved to a personal computer and the like so that analysis can be performed using the personal computer.

In addition, the main body unit may be provided with a function for automatically adjusting time of the timer by communicating with an external unit. As a function for automatically adjusting the time, there is NTP for example. In this case, the main body unit is provided with a communication connector and a network communication function. As the communication connector, a USB connector, a RS-232C D-sub 15 pin connector, a LAN RJ-45 connector and the like can be used. By the way, by using an after-mentioned wireless communication function, it is also possible to automatically adjusting time using GPS radio wave or standard radio wave.

Accordingly, by providing the function for automatically adjusting time, it becomes possible to ascertain a blood pressure value at an accurate time.

In addition, the main body unit may be provided with a communication connector such as the USB connector, the RS-23sC D-sub 15 pin connector, LAN RJ-45 connector and the like, so as to output a measurement value stored in the memory to outside of the main body unit without removing the memory. In addition, it can be also configured to output the measurement value stored in the memory to outside of the main body unit using wireless communications. In this case, the main body unit is provided with a wireless communication unit. As a function of the wireless communication unit, Bluetooth, weak wireless, particular power saving wireless, wireless LAN (802.11b, 802.11a, 802.11g, etc.) and the like can be used.

By providing such a function for outputting the measurement result by wireless, a blood pressure value of a measurement subject can be monitored remotely.

The above-mentioned memory and the technique of the communication function themselves are well-known techniques, and can be easily implemented into a blood-pressure meter by a person skilled in the art.

According to the above-mentioned ear-type blood-pressure meter, by measuring blood pressure on the ear, a pressing area is much smaller than that when using the upper arm for measurement. Thus, load for a measurement subject when measuring the blood pressure can be largely decreased compared with other type (arm type and the like). In addition, since the heights of the ear and the heart are scarcely changed in a daily life in positions of standing, sitting and the like other than lying, measurement error can be largely reduced compared with that of the upper arm. Thus, according to this configuration, a blood-pressure meter that can measure and record blood pressure continuously for more than 24 hours can be provided.

(Configuration for Recording Behavior History)

In the following, a blood-pressure meter having a configuration for recording behavior history is described as an embodiment of the present invention. This blood-pressure meter has functions for recording a blood pressure measurement result to the storing unit adding year/month/date/hour/minute/second information, and recording behavior history of a measurement subject with a blood pressure value to the storing unit while adding year/month/date/hour/minute/second information.

Figure 9:
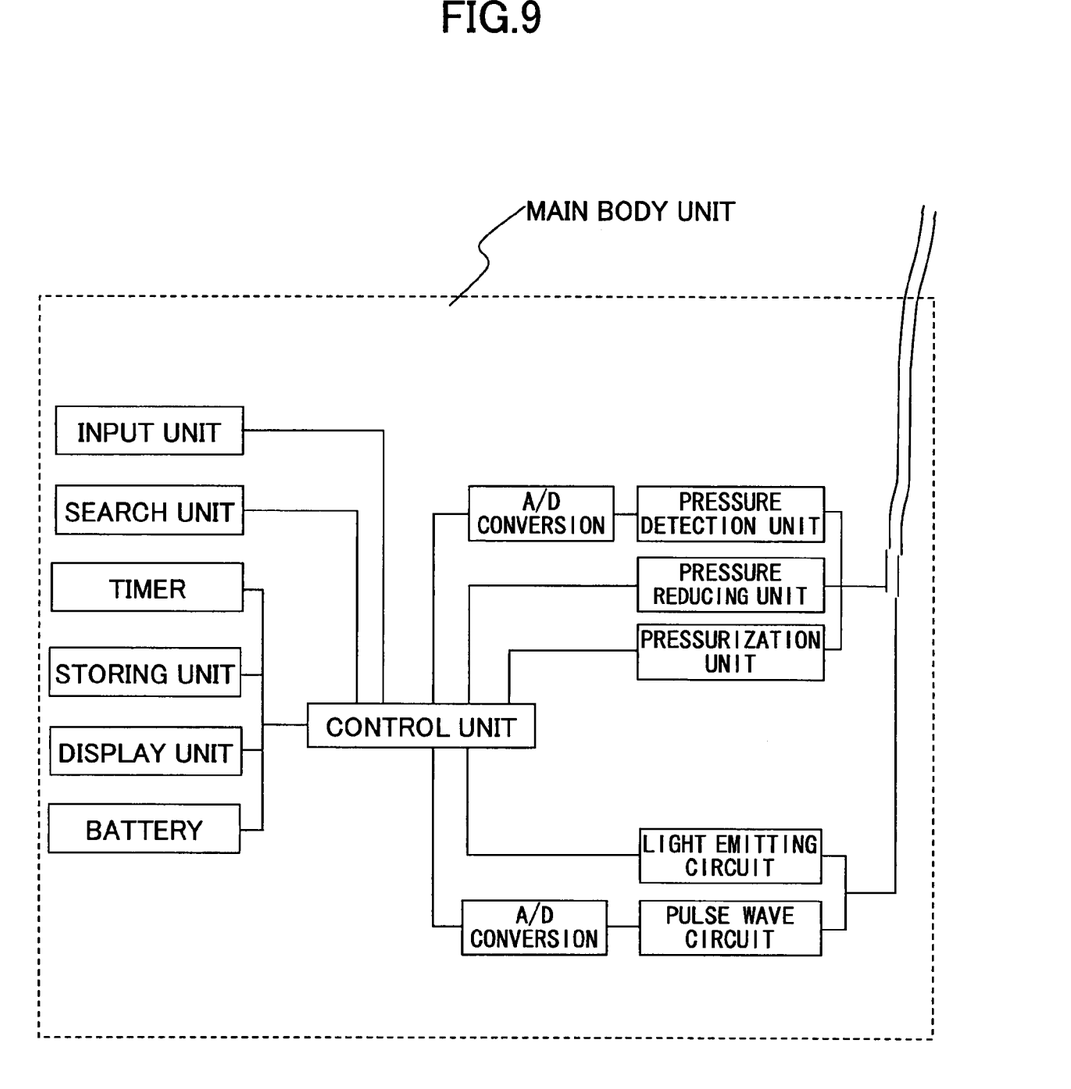
FIG. 9 shows a configuration example of the main body unit of the blood-pressure meter in an embodiment of the present invention.

FIG. 9 shows a configuration example of the main body unit. As shown in FIG. 9, compared to the basic configuration of FIG. 3, an input unit for data input and a search unit for data search are additionally provided. The input unit includes a keyboard or buttons and the like. Also, as the input unit, a mechanism can be used for directly inputting from the liquid crystal display that is the display unit.

Figure 10:
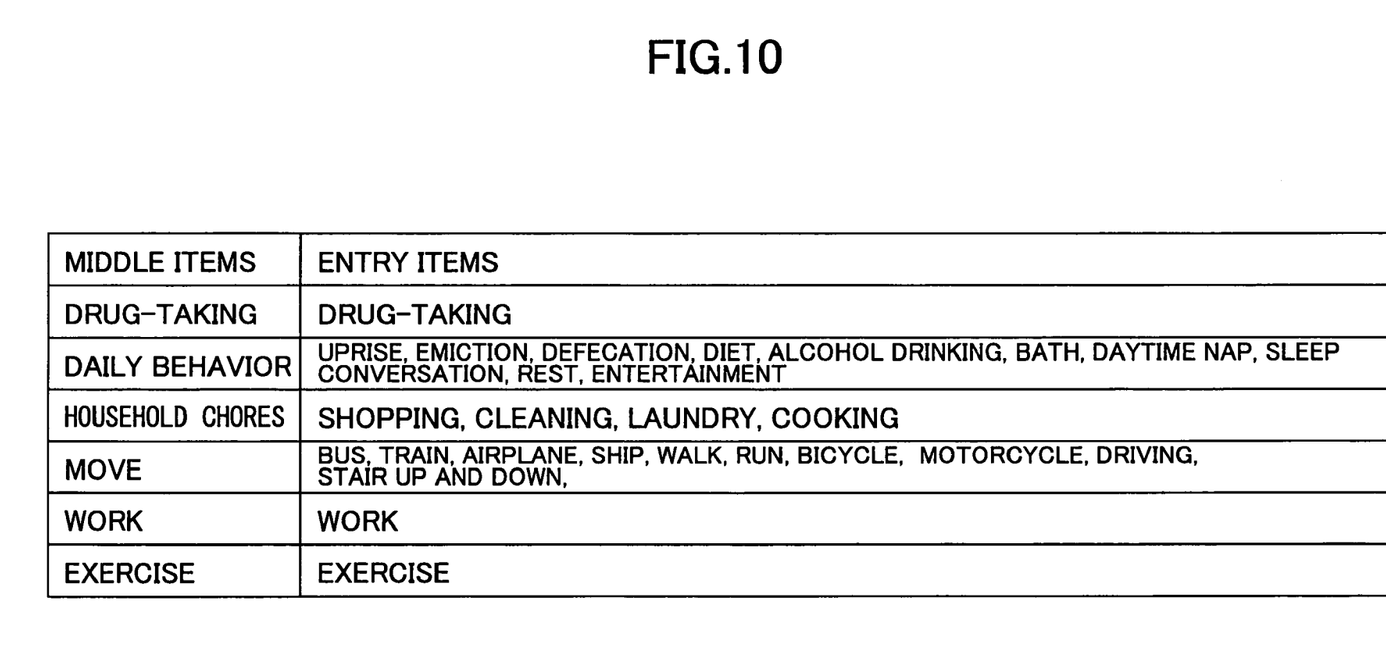
FIG. 10 is a drawing showing examples of items entered into the blood-pressure meter.

In this embodiment, entering items are displayed on the display unit so that selection is performed using the input unit. For example, an middle item is selected, and further an entering item is selected using a pull down menu and the like. Of course, behavior information may be directly entered without using menu selection. FIG. 10 shows an example of the selection items. As items for entering subjective symptoms, there are "chest pain", "heartbeats", "breathlessness", "vertigo", "malaise" and the like.

A current time (including year/month/date/time/minute/second information) output from the timer is added to entering data, and the entering data with the current time is stored in the storing unit. Instead of automatically adding the time, the current time may be entered manually. The user can select between automatic input and manual input.

Accordingly, since the behavior history can be stored while the time being associated with the behavior history, it can be easily ascertained that each blood pressure value that is measured at constant time intervals and stored by being associated with the time corresponds to what behavior. By the way, the process for storing the behavior history while being associated with the time into the storing unit, and the process for storing the blood pressure measurement result while being associated with the time into the storing unit are executed under control of the control unit.

The behavior history and data of the blood pressure value stored in the storing unit can be searched under various conditions and can be displayed. For example, by entering a range of blood pressure values, a search result (year/month/date/time/minute/second, behavior history, symptoms, systolic pressure value, diastolic pressure value and the like) within the range is displayed in chronological order.

More particularly, for example, it is possible to enter "systolic pressure is equal to or greater than XXX" and "diastolic pressure is equal to or greater than XXX" and perform a search under AND condition or OR condition between them. The user can select between AND or OR. In addition, a search can be performed under AND or OR for "systolic pressure is equal to or less than XXX" and "diastolic pressure is equal to or less than XXX". By the way, for entering the condition such as "systolic pressure is equal to or greater than XXX", numerals can be directly entered, or the blood-pressure meter may be configured to be able to select a condition using a pull down menu and the like.

In addition, by entering a particular behavior history as a search keyword, a search is performed using the behavior history as a key so that a search result (year/month/date/time/minute/second, symptoms, systolic pressure, diastolic pressure and the like) can be displayed in chronological order. In addition, a symptom can be used as a search keyword.

In addition to using the search unit for performing the above-mentioned search process, the above-mentioned search process can be also performed by providing a search program in the storing unit and executing the search program by the control unit.

As mentioned above, although various kinds of searches can be performed, the search is not necessarily performed in the blood-pressure meter. For example, by sending data of the behavior history, the blood pressure values and times corresponding to them to a personal computer using the method described in the first embodiment, the searches can be performed in the personal computer.

Conventionally, there was a problem in that complicated work was necessary such as recording behavior history onto a paper by hand and comparing the record with blood pressure values after that. According to the present embodiment, the problem can be solved. In the present embodiment, although the ear-type blood pressure is taken as an example, the configuration for recording the behavior history with time can be also applied to one other than the ear-type blood-pressure meter.

(Configuration for Performing Blood Pressure Measurement Based on Degree of Activity Etc.)

Next, an example of a blood-pressure meter further including a configuration for performing blood pressure measurement based on degree of activity and the like is described. In this embodiment, the blood-pressure meter is provided with a sensor for detecting the degree of activity. Then, the blood-pressure meter detects physical load from the degree of activity and starts blood pressure measurement being triggered by detection of the load. By adopting such a configuration, it becomes possible to easily ascertain relationship among the degree of activity, the blood pressure and the behavior history.

Figure 11:
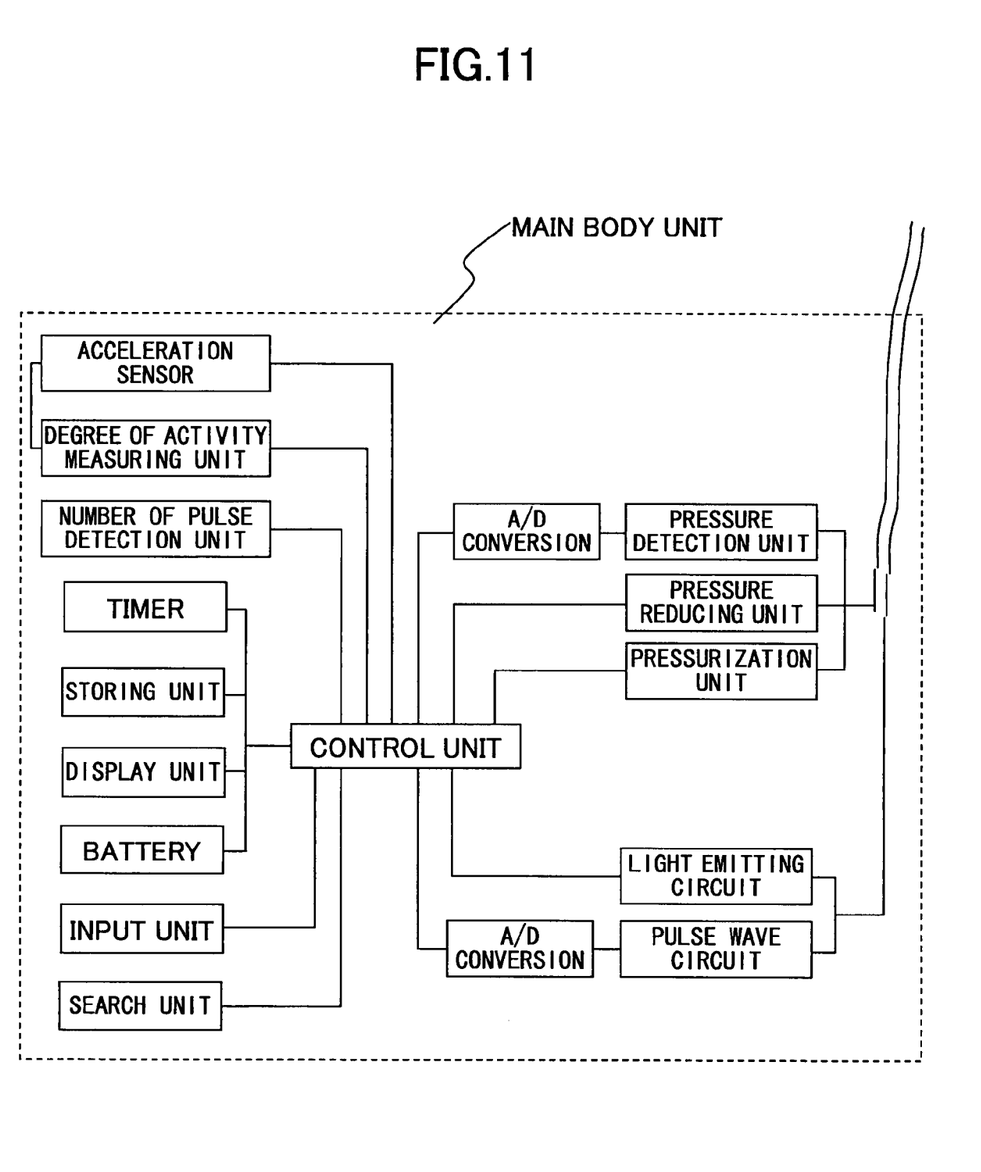
FIG. 11 shows another configuration example of the main body unit of the blood-pressure meter in an embodiment of the present invention.

FIG. 11 shows a configuration example of the main body unit of the blood-pressure meter in this case. As a sensor for detecting the degree of activity, an acceleration sensor is provided in the main body unit (or in the measuring unit). By the way, the acceleration sensor is not necessarily placed in the blood-pressure meter. The acceleration sensor may be attached anywhere as long as activity of the measurement subject can be detected. In this case, the acceleration sensor and the main body unit is connected by a signal line.

In addition to the acceleration sensor, a degree of activity measuring unit and a number of pulse detection unit are provided. The degree of activity measuring unit includes a function for detecting a number of steps taken by the measurement subject per unit time. In this embodiment, the number of steps taken per unit time is regarded to be the "degree of activity". Although the unit time can be freely set, it is set to be five minutes, for example. By the way, the degree of activity is not limited to the number of steps taken per unit time, and any amount can be used as the degree of activity as long as the amount indicates degree of activity of a human.

The number of pulse detection unit includes a function for detecting a number of pulses based on the pulse wave detected by the pulse wave circuit.

By using the blood-pressure meter having such configuration, measurement is automatically started when the degree of activity is equal to or greater than a preset threshold, and after that, blood pressure is measured at predetermined constant time intervals for a predetermined time period, or a predetermined number of times. More particularly, the threshold is stored in the storing unit beforehand. Then, the degree of activity measuring unit refers to the value, and instructs the control unit to start measurement of blood pressure when the degree of activity becomes equal to or greater than the value. Then, the control unit instructs each function unit for performing measurement of blood pressure to operate.

A measured result is displayed by the display unit, and is stored in the storing unit with measurement time and the value of the degree of activity at the time when the measurement is performed. Accordingly, it becomes possible to perform measurement of blood pressure in a situation in which physical load is applied.

For performing such operation using a conventional blood-pressure meter for continuously measuring blood pressure, complicated work is necessary for measuring blood pressure continuously for a long time and comparing the degree of activity and the measured blood pressure value after measurement. In addition, since it is necessary to measure blood pressure continuously for a long time, problems of burden for the measurement subject and lack of battery capacity may occur. On the other hand, according to the blood-pressure meter of this embodiment, such problem can be solved.

The measurement may be automatically started when the degree of activity is equal to or less than a predetermined threshold. Accordingly, blood pressure measurement can be performed in a situation in which physical load is not applied.

In addition, by using the number of pulse detection unit, measurement can be automatically started when the degree of activity is equal to or less than a predetermined threshold and the number of pulses is equal to or greater than a predetermined number of pulses. When the degree of activity is low and the number of pulses is high, it can be considered to be in a status in which mental load is applied. Thus, by performing measurement by such method, it becomes possible to perform blood pressure measurement under a status in which mental load is applied.

In addition, the blood-pressure meter may be configured such that measurement automatically starts when the degree of activity is equal to or less than a predetermined threshold and the number of pulses is equal to or less than a predetermined number of pulses. Accordingly, it becomes possible to perform measurement in a state in which neither physical load nor mental load is applied.

Combination of the degree of activity and the number of pulses that is used as a starting trigger of blood pressure measurement is not limited to the above-mentioned examples, and the combination can be set freely. For example, following conditions can be adopted: "the degree of activity is equal to or greater than a predetermined threshold and the number of pulses is equal to or greater than a predetermined number of pulses", "the degree of activity is equal to or greater than a predetermined threshold and the number of pulses is equal to or less than a predetermined number of pulses", "the degree of activity is equal to or less than a predetermined threshold or the number of pulses is equal to or greater than a predetermined number of pulses", "the degree of activity is equal to or less than a predetermined threshold or the number of pulses is equal to or less than a predetermined number of pulses", "the degree of activity is equal to or greater than a predetermined threshold or the number of pulses is equal to or greater than a predetermined number of pulses", "the degree of activity is equal to or greater than a predetermined threshold or the number of pulses is equal to or less than a predetermined number of pulses".

By the way, in each of the above-mentioned measurement methods, in a case where a state that triggers the start of the blood pressure measurement continues for a long time, the measurement may be performed at regular intervals, for example. In addition, setting for using a particular measurement method among the measurement methods can be performed from the input unit provided in the main body unit.

According to this embodiment, an abnormality such as one in which blood pressure does not increase although the degree of activity is high can be detected without measuring blood pressure continuously for a long time. In addition, since the ear-type blood-pressure meter that is held at an ear part is used, blood pressure can be measured even in activity such as during walking so that the relationship between the degree of activity and the blood pressure can be ascertained easily. These were not realized by a conventional ABPM blood-pressure meter.

By the way, processes in the main body unit in the embodiments described so far may be realized using a program. In that case, the program is stored in the storing unit and the control unit (corresponding to a CPU of a computer) executes the program so as to realize processes of the degree of activity measuring unit, the number of pulses detection unit, the display unit, the input unit, the search unit and the like. For example, the program is stored in a read/write memory, and by setting the memory into the blood-pressure meter, the program is executed by the main body unit. In addition, as a recording medium for storing the program, a floppy disk and a CD-ROM and the like can be used other than the above-mentioned memory.

The present invention is not limited to the specifically disclosed embodiments, and variations and modifications may be made without departing from the scope of the present invention.

The invention claimed is:

1. An ear blood-pressure meter comprising:
   storing means for storing a blood pressure measurement result;
   time measurement means for measuring a time;
   input means for receiving behavior history;
      means for storing the blood pressure measurement result into the storing means while associating the blood pressure measurement result with a time when blood pressure measurement is performed;
      means for storing the behavior history into the storing means while associating the behavior history with a time corresponding to the behavior history;
   a pair of cuffs adapted to apply pressure directly onto opposite surfaces of a tragus or a periphery of the tragus in a temporal region;
   a pair of opposed arms linked together at one end of each arm by a spindle;
   a first air tube connected to one of the cuffs, the first air tube extending through a first end of a first arm of the pair of opposed arms and exiting through a second end of the first arm;
   a second air tube connected to another of the cuffs, the second air tube extending through a first end of a second arm of the pair of opposed arms and exiting through a second end of the second arm;
   a distance variable mechanism arranged to adjust a distance between ends of the arms remote from the spindle by changing an angle between the spindle and one of the arms, the cuffs being attached to their respective arms at the remote ends thereof;
   a detector configured to detect a pulse wave at the tragus or tragus periphery, the detector including a light-emitting element and a light receiving element, and both the light-emitting element and the light-receiving element are located on a same expanding surface of one of the cuffs, so as to be pressed in use against the tragus or tragus periphery; and
   a controller configured to control the cuffs to increase or decrease pressure applied onto the tragus or tragus periphery,
   wherein the ear blood pressure meter is adapted to measure blood pressure by pinching the tragus or tragus periphery between the cuffs to compress blood vessels.

2. The ear blood-pressure meter as claimed in claim 1, further comprising:
   display means for displaying candidates for being entered as the behavior history.

3. The ear blood-pressure meter as claimed in claim 1, wherein the ear-type blood-pressure meter performs blood pressure measurement at predetermined time intervals by measuring the predetermined time intervals by the time measurement means.

4. The ear blood-pressure meter as claimed in claim 1, further comprising:
   search means for searching blood pressure measurement results and behavior history stored in the storing means based on a condition received from the input means to extract data satisfying the condition.

5. The ear blood-pressure meter as claimed in claim 4, wherein the search means extracts information including a blood pressure value corresponding to behavior information received from the input means.

6. The ear blood-pressure meter as claimed in claim 4, wherein the search means extracts information including behavior history corresponding to a blood pressure value received from the input means.

7. The ear blood-pressure meter as claimed in claim 1, wherein the cuffs are connected to a mechanism using air or an actuator.

8. The ear blood-pressure meter as claimed in claim 1, wherein the detector includes a pressure sensor, a vibration sensor, and a microphone for measuring Korotkoff sound.

9. An ear blood-pressure meter comprising:
   a memory that stores a blood pressure measurement result;
   an input unit that receives a behavior history;
      a controller that stores the blood pressure measurement result into the memory while associating the blood pressure measurement result with a time when blood pressure measurement is performed, and said controller also stores the behavior history into the memory while associating the behavior history with a time corresponding to the behavior history;
   a pair of cuffs adapted to apply pressure directly onto opposite surfaces of a tragus or a periphery of the tragus in a temporal region;
   a pair of opposed arms linked together at one end of each arm by a spindle;
   a first air tube connected to one of the cuffs, the first air tube extending through a first end of a first arm of the pair of opposed arms and exiting through a second end of the first arm;
   a second air tube connected to another of the cuffs, the second air tube extending through a first end of a second arm of the pair of opposed arms and exiting through a second end of the second arm;
   a distance variable device arranged to adjust a distance between ends of the arms remote from the spindle by changing an angle between the spindle and one of the arms, the cuffs being attached to their respective arms at the remote ends thereof;
   a detector configured to detect a pulse wave at the tragus or tragus periphery, the detector including a light-emitting element and a light receiving element, and both the light-emitting element and the light-receiving element are located on a same expanding surface of one of the cuffs, so as to be pressed in use against the tragus or tragus periphery; and
   a controller configured to control the cuffs to increase or decrease pressure applied onto the tragus or tragus periphery,
   wherein the ear blood pressure meter is adapted to measure blood pressure by pinching the tragus or tragus periphery between the cuffs to compress blood vessels.

* * * * *